United States Patent [19]
Brooks et al.

[11] 4,449,408
[45] May 22, 1984

[54] EMAT TEST APPARATUS HAVING RETRACTABLE PROBE

[75] Inventors: Robert A. Brooks, Rye, N.Y.; Terrance R. Banach, Danbury, Conn.; Erik Barman, Spring Valley; Michael R. Livia, Brooklyn, both of N.Y.

[73] Assignee: Magnetic Analysis Corporation, Mt. Vernon, N.Y.

[21] Appl. No.: 370,831

[22] Filed: Apr. 22, 1982

[51] Int. Cl.³ .............................................. G01N 29/04
[52] U.S. Cl. ........................................ 73/643; 324/226
[58] Field of Search .................... 73/643; 324/226, 227

[56] References Cited
U.S. PATENT DOCUMENTS

| | | | |
|---|---|---|---|
| 3,460,063 | 8/1969 | Houck et al. | 340/15 |
| 3,583,213 | 6/1971 | Houck et al. | 73/67.5 |
| 4,149,421 | 4/1979 | Bottcher | 73/643 |

FOREIGN PATENT DOCUMENTS 54-8585  1/1979  Japan ..................................... 73/643

OTHER PUBLICATIONS

"EDW-T Electrodynamic Transducer", of NUKEM GmbH.

Primary Examiner—Howard A. Birmiel
Attorney, Agent, or Firm—James J. Daley

[57] ABSTRACT

An electromagnetic acoustic wave transducer (EMAT) probe is supported with its magnetic field issuing device for movement from a retracted position into closely spaced relation to a test object. Relative movement is provided as between a magnetic flux coupler and the EMAT field issuing device to derive the EMAT magnetic field from a magnet. A biasing unit urges the probe into its retracted position and the probe is moved into its operative position by magnetic interaction with a test object.

13 Claims, 4 Drawing Figures

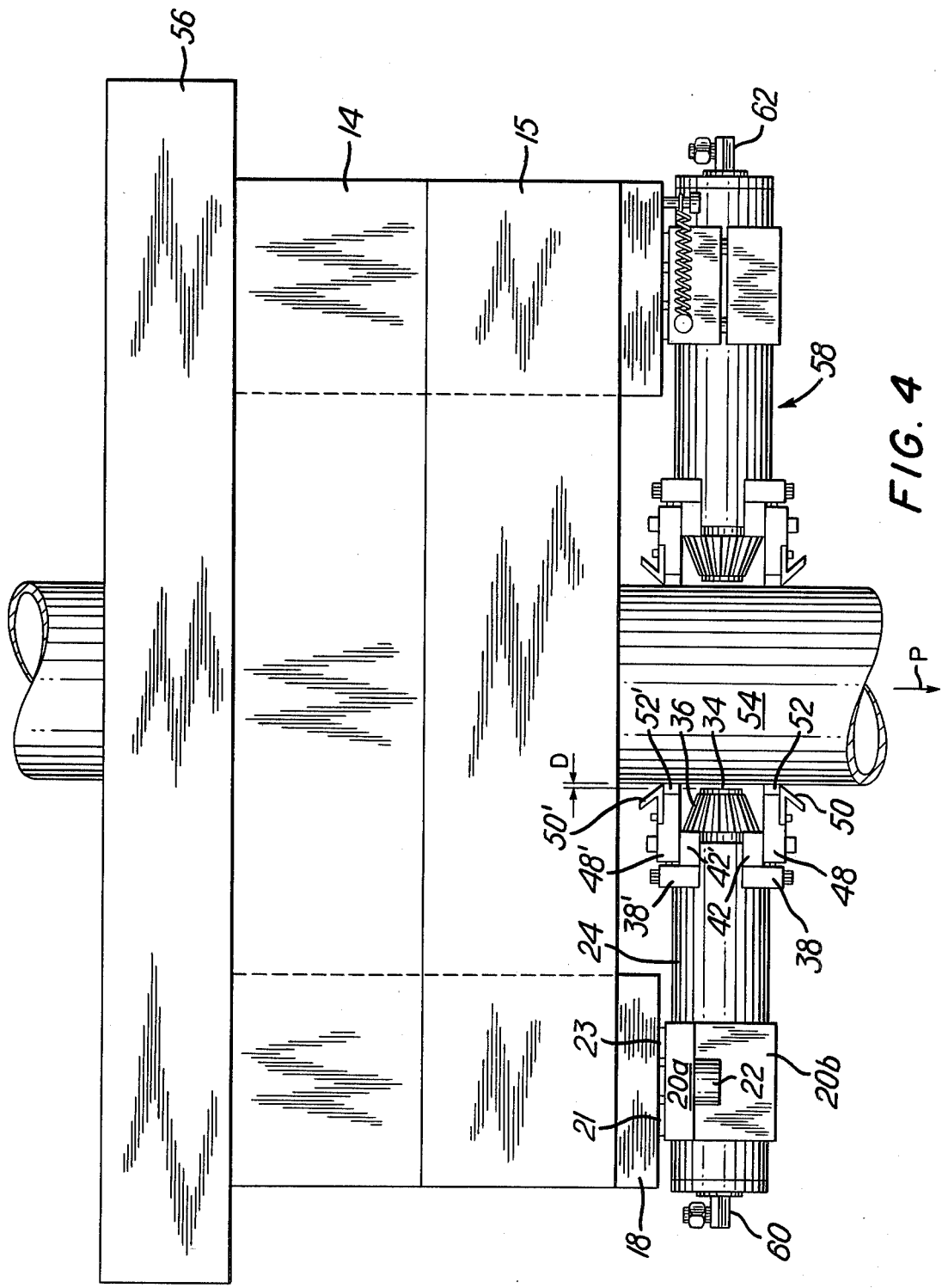

EMAT TEST APPARATUS HAVING RETRACTABLE PROBE

FIELD OF INVENTION

This invention relates generally to nondestructive testing of objects and pertains more particularly to examination of objects by ultrasonic apparatus and methods.

BACKGROUND OF THE INVENTION

Each of the several techniques for nondestructive object testing, namely, leakage flux detection, eddy current measurements and ultrasonic wave examination, has unique applicability in comparison with the others in accordance with the diverse parameters of that particular testing situations. However, the application of ultrasonic techniques inherently is more difficult than the other methods based principally upon the need in present commercial ultrasonic apparatus for a fluid couplant medium between the object under test and a piezoelectric transducer transmitting and receiving the ultrasonic wave. Thus, in certain instances, in which one would prefer to employ the ultrasonic technique, he elects one of the other practices or foregoes testing if the use of a couplant is not permitted.

Observation of the phenomenon of electromagnetically inducing an acoustic wave in an object under steady-state magnetic field influence as described, for example, in U.S. Pat. Nos. 3,460,063 and 3,583,213, has not given rise to any substantial change on the commercial ultrasonic testing scene, despite elimination of the bothersome couplant medium. Thus, while a wide variety of EMAT (electromagnetic acoustic transducer) systems have become known, such as that shown in the '063 and '213 patents, SAW (surface acoustic wave) transducers described in the literature, and the like, the industry-wide impact thereof is not readily seen. From applicants' viewpoint, the industry presently lacks a commercially viable system environment for effective use of EMAT probes in the testing of moving objects, particularly thin-walled pipes and the like.

Two aspects of EMAT object testing, as constrasted with leakage flux testing, are considered particularly relevant to this situation. Peculiar to EMAT test apparatus is the need for it to provide a strong magnetic bias field at the transduction surface, i.e., the object surface to which the electromagnetic acoustic wave is applied. Conversely, leakage flux detecting transducers are passive, i.e., do not generate but simply detect flux issuing at an object flaw. Accordingly, air gap minimization and constancy is more critical to EMAT test apparatus. Further, leakage flux detecting transducers may include protective metal between detector coils and the object, which metal may ride upon the object during testing and otherwise protect the transducer from damage by the object during insertion of the object for testing. To the contrary, the EMAT probe with its transmitting and receiving coils must be contiguous with the transduction air gap, without intervening metallic protection. Given these aspects of EMAT object testing, some basis is perceived for the commercially lagging status thereof as against systems of the other testing categories above noted.

SUMMARY OF THE INVENTION

The present invention has as its primary object the provision of improved EMAT apparatus and enhanced methods for object testing by electromagnetic acoustic wave usage.

A more particular object of the invention is to provide for effective electromagnetic acoustic wave testing of moving objects.

In attaining these and other objects, the invention provides apparatus for EMAT object testing which minimizes and renders constant the transduction surface air gap and also affords enhanced protection of the EMAT coils during object insertion for test and testing. Further, the invention provides a method for testing wherein insertion of a test object into residence in the apparatus effects operating registration of the EMAT transducer and the magnetic field generator with the object.

Apparatus in accordance with the invention includes a flux coupler fed by a magnet or electromagnetic system and a flux receiving and issuing member which supports an EMAT transducer. The flux receiving and issuing member and the flux coupler are supported for movement relative to one another, whereby the EMAT transducer may be retained in an inoperative position when a test object is not present and magnetically moved therefrom into operative position by interaction of flux issuing from the EMAT supporting member and the object. Guard and gap defining means extend outwardly of the EMAT coils for engaging the object.

In its particularly preferred embodiment, the apparatus includes a first plate member functioning as a flux coupler and a second plate member pivotally movable relative to the first plate member and supplying flux therefrom to a pole piece circumscribingly supporting the EMAT probe and also supporting the guard and gap defining means. The flux issuance direction of the pole piece is aligned with the directional transduction sense of the EMAT. A bias spring engages the plate member to bias the pole piece in a direction opposite the flux issuance direction, whereby the EMAT probe is maintained distal from the path of object insertion when a test object is not present. Spring force is selected to be less than the magnetic force of attraction between the pole piece and object to permit magnetic influence of override.

The foregoing and other features of the invention will be further understood from the following detailed description of the preferred embodiment and by reference to the drawings wherein like reference numerals identify like parts throughout.

DESCRIPTION OF THE DRAWINGS

FIG. 4 is a complete top plan view of the FIG. 1 apparatus, shown with support for rotative movement thereof about a test object in the form of a thin-walled metal pipe.

DESCRIPTION OF PREFERRED EMBODIMENTS

Figure 1:
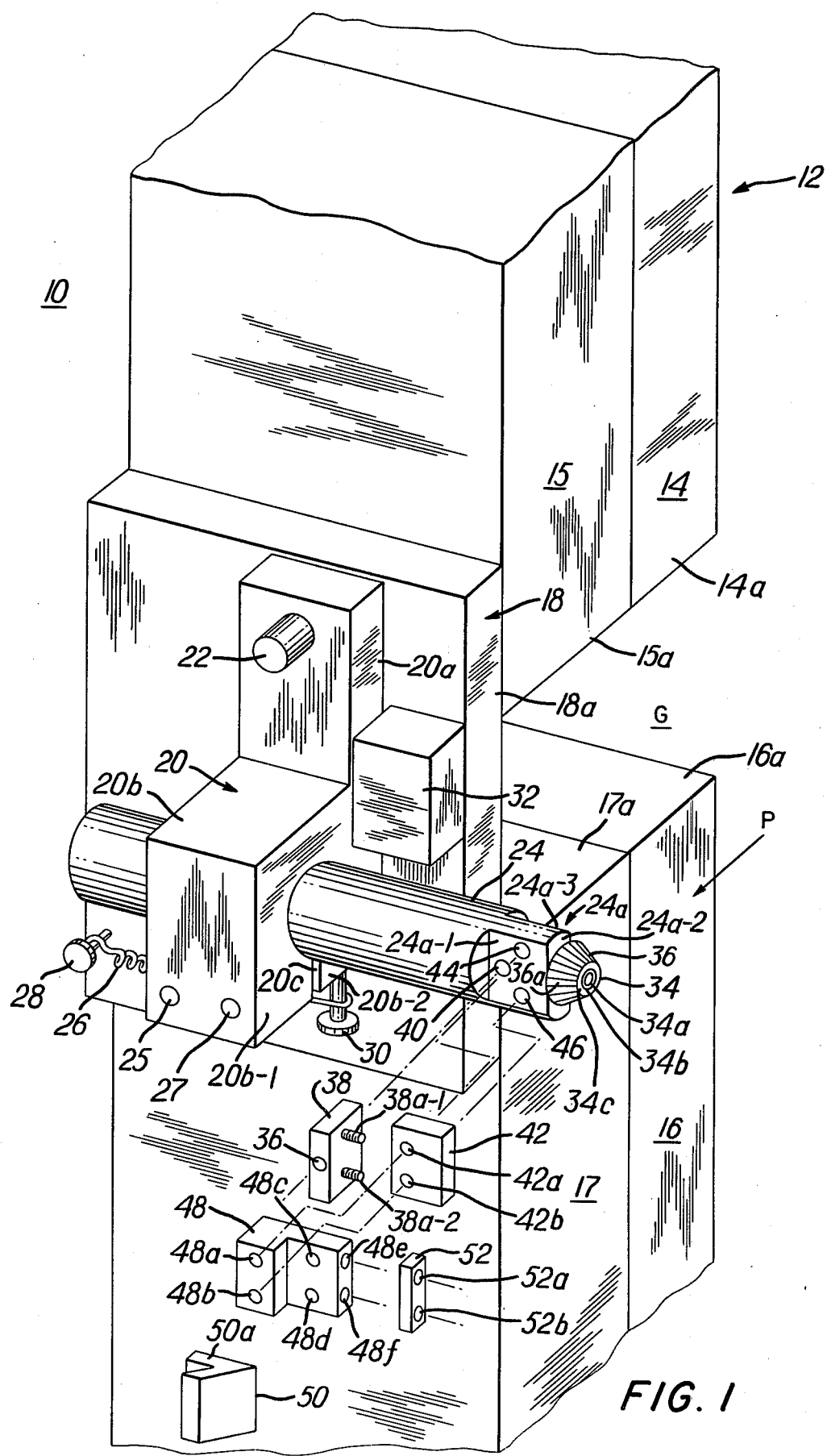
FIG. 1 is a partial perspective view of apparatus in accordance with the invention with the EMAT probe and pole piece shown in operative position, the EMAT guard and gap control means being shown in exploded fashion to indicate assembly and structural detail.
Figure 2:
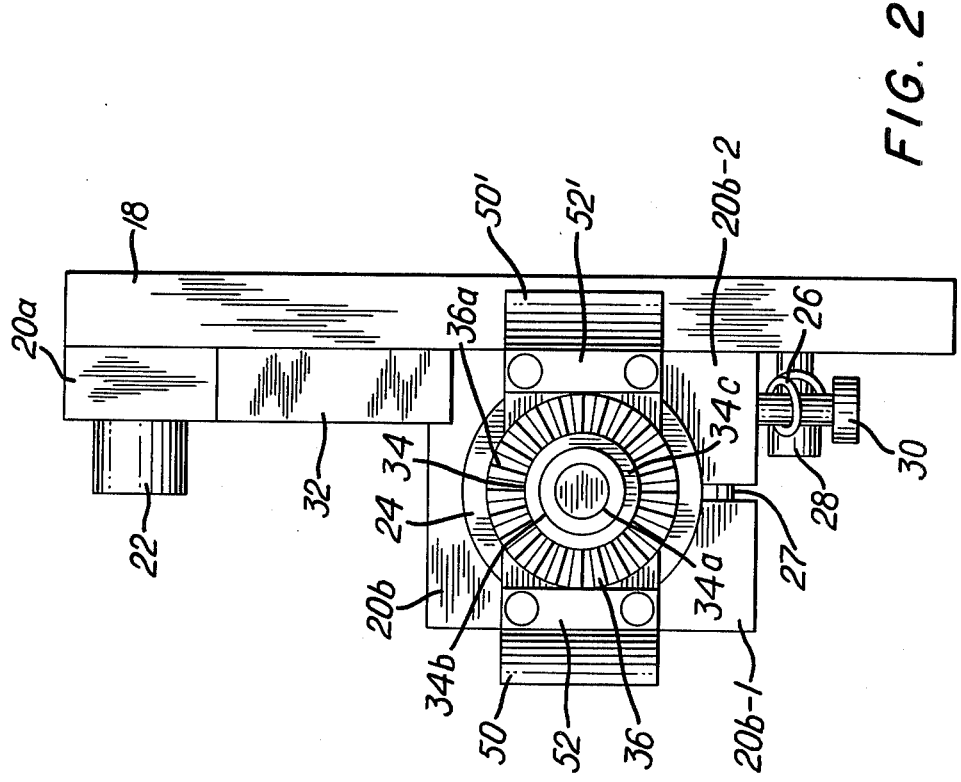
FIG. 2 is an elevational view as would be seen righwardly of FIG. 1 with the guard and gap control means assembled.

Referring to FIGS. 1 and 2 electromagnetic acoustic wave object examination apparatus 10 includes steady-state or quasi-static magnetic field generating means 12 having half cylindrical elements 14, 15, 16 and 17 defining respective pole faces 14a, 15b, 16a, and 17a aside air gap G. Magnetic flux coupler 18 spans elements 14 and 16 vertically and is suitably mechanically secured thereto in fixed disposition.

Magnetic flux receiving and issuing unit 20 is supported for movement relative to coupler 18 through the agency of pivotal support pin 22, threadably secured in coupler 18 and providing an interior bearing surface for unit 20. Referring to FIG. 4, non-magnetic members 21 and 22 provide exterior bearing surfaces between coupler 18 and unit 20 and provide a controlled air gap therebetween.

In the illustrated embodiment, coupler 18 is a plate member 18a and unit 20 includes as a component thereof plate member 20a having pole piece support 20b integrally formed therewith and including depending pole piece support grippers 20b-1 and 20b-2, spaced apart by slot 20c. Pole piece 24 is releasably securable in support 20b, threadable members 25 and 27 being insertable through gripper 20b-1 into suitably interiorly threaded slots in gripper 20b-2 for securement of pole piece 24 on apparatus assembly and for release thereof to adjust the pole piece for different sized test objects.

For purposes of controlling the relatively positioning of coupler 18 and unit 20, apparatus 10 includes a biasing device, preferably in the form of spring 26, secured at one end to post 28 seated in coupler 18 and at the other end to post 30 extending from gripper 20b-2. The biasing device is overcome by magnetic interaction between pole piece 24 and an object to be examined, as discussed below, at which point cushion stop block 32, secured upon plate member 18a, engages plate member 20a to eliminate overtravel thereof.

Pole piece 24 has a reduced rightward portion 24a which has vertical sides 24a-1 and 24a-2 and tapered forward wall 24a-3. EMAT probe 34 preferably is comprised of a pair of concentrically arranged coils 34a and 34b, supported in a flat synthetic plastic casing 34c. A commercially available version of usable transducer is incorporated in an EMAT probe available from NUKEM GmbH of Germany as Electrodynamic Transducer EDW-T. Casing 34c is circumscribed by frusto-conical metal end member 36, serrated as indicated by slits 36a at fifteen degree circumferential intervals.

Turning now to the exploded component showings in FIG. 1, and the assembled showings thereof in FIGS. 2 and 4, adjusting block 38 supports set screws 38a-1 and 38a-2 for trimming the position of guard 48 and includes throughbore 38b registrable with pole piece threaded bore 40. Filler piece 42 nests behind end member 36 and abuts block 38 and has throughbores 42a and 42b registrable with pole piece threaded bores 44 and 46.

Guard support 48 has throughbores 48a and 48b registrable with bores 42a and 42b of filler piece 42 and includes a recessed land 48c for seating of sideguard 50. Sideguard 50 has throughbores (not shown) extending through arm 50a and registrable with threaded bores 48c and 48d of support 48. End guard 52, preferably a carbide, has throughbores 52a and 52b registrable with threaded bores 48e and 48f of support 48. Screws provide assembly of the components as indicated in FIGS. 2 and 4, which also show the counterpart opposite side components 38', 42', 48', 50' and 52', omitted from the FIG. 1 showing for clarity of presentation.

As assembled and in operative position, carbides 52 and 52' engage a test object 54 (FIG. 4), spacing EMAT probe 34 therefrom by distance D, i.e., the transduction air gap, which is desirably about one and one-half millimeters. Further, together with sideguards 50 and 50', the carbides protect the EMAT probe from damage from the test object during its movement into operative position.

Figure 3:
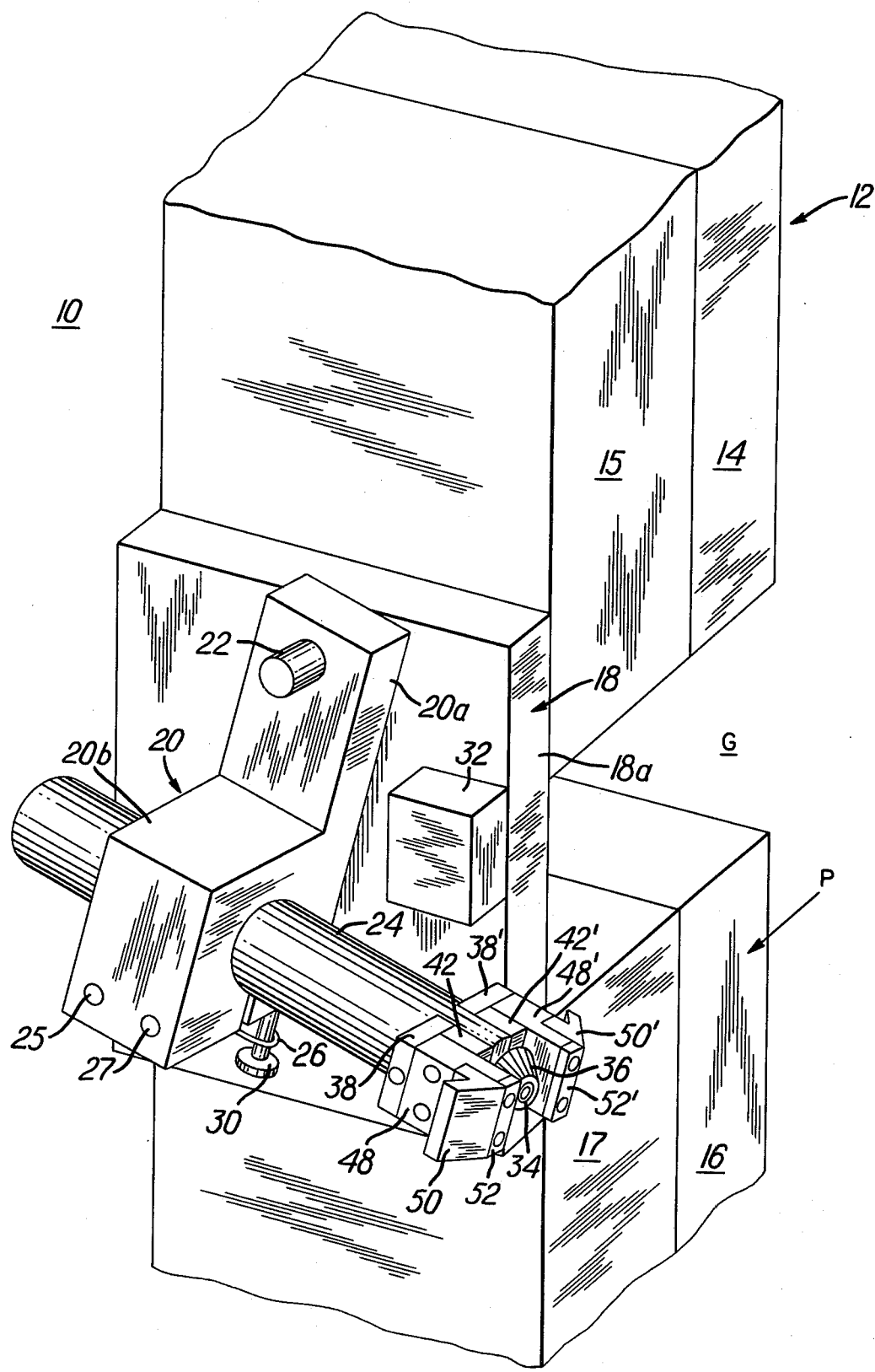
FIG. 3 is a further partial perspective view of the FIG. 1 apparatus with the EMAT probe and pole piece being retracted to an inoperative position.

Referring now to FIG. 3, flux receiving and issuing unit 20 is shown in its retracted or inoperative and path-distal position, some twenty degrees off vertical. In its method aspects, the invention provides for biasing unit 20 into such inoperative position by a force oppositely directed from the direction of magnetic force on unit 20 through interaction of flux issuing therefrom and an object in path P. The bias force provided by spring 36 is selected to be of sufficient magnitude to so bias unit 20. It is, however, less than the magnetic force required to provide magnetic field interaction with the path when the pole piece is in such path-distal position. Accordingly, pole piece 24 and EMAT probe 34 are movable with unit 20 into operative position responsively to the advance of an object in path P into the vicinity of retracted unit 20.

In complete top plan view of FIG. 4, upper magnets 14 and 15 and the unshown lower magnets 16 and 17 are secured to head plate 56 which is preferably supported for rotation about path P by a rotating head arrangement, such as is shown in commonly-assigned U.S. Pat. No. 3,854,085, issued on Dec. 10, 1974, to which incorporating reference is hereby made, or as may be seen in commercial flux leakage test products of Magnetic Analysis Corporation, e.g., Rotoflux Type 1600. Also seen in FIG. 4 is a second EMAT apparatus 58, identical to the EMAT apparatus of FIG. 1 but inverted such that rotational movement of its EMAT probe and pole piece into its illustrated position is of opposite sense from that of the FIG. 1 apparatus. Electrical connections are made through connector pairs 60 and 62 for furnishing radio frequency excitation to transmitting coil 34a (FIG. 1) of EMAT probe 34 and for processing the output signals of coil 34b. This wound coil typically has fifteen turns and receiving coil 34b typically has one to three hundred turns. Excitation is typically pulsed three hundred volts at radio frequency, these parameters being selected on balance in conjunction with magnetic field strength and magnitude of flux provided to the object at the transduction surface and the characteristics of the object. These matters, as well as underlying theory and received signal processing practices are set forth in part in U.S. Pat. Nos. 3,583,213 and 3,460,063 referred to above and otherwise in published literature, to which reference may be made.

Various changes may evidently be made to the foregoing particularized embodiment and practice without departing from the invention. Thus, while the relative movement as between flux coupling device 18 and flux receiving and issuing unit 20 has been indicated as pivotal movement and the locus of such movement being an arcuate path intersecting object path P, the invention of course encompasses other types of motion. Likewise, EMAT probe 34 may take configuration other than as indicated. Accordingly, the depicted preferred embodiment is intended in an illustrative and not in a limiting sense. The true spirit and sope of the invention are set forth in the following claims.

We claim:

1. Apparatus for electromagnetic acoustic wave examination of an object, comprising:
   (a) means for generating a magnetic field;
   (b) flux coupler means fixedly disposed relative to said field generating means for coupling magnetic flux therefrom;
   (c) flux receiving and issuing means supported for movement relative to said flux coupler means for receiving magnetic flux therefrom in such movement and directionally issuing such received flux; and
   (d) transducer means for electromagnetic generation of an acoustic wave supported with said flux receiving means for movement therewith.

2. The apparatus claimed in claim 1 wherein said flux coupler means and said flux receiving and issuing means include respective first and second plate members mutually pivotally moveable to effect such relative movement between said flux coupler means and said flux receiving and issuing means.

3. The apparatus claimed in claim 2 wherein said second plate member is supported by said first plate member for such pivotal movement therebetween.

4. The apparatus claimed in claim 1 wherein said flux receiving and issuing means includes a pole piece for issuing said received flux in a predetermined direction.

5. The apparatus claimed in claim 4 wherein said transducer means is supported relative to said pole piece such that the directional transduction sense of said transducer means is aligned with such predetermined flux issuance direction of said pole piece.

6. The apparatus claimed in claim 5 including means supported by said pole piece and extending therefrom beyond said transducer means both for guard protection of said transducer means and for definition of air gap as between said transducer means and an object to be examined.

7. The apparatus claimed in claim 5 wherein said pole piece is releasably secured in said flux receiving and issuing means for selective variable positioning of said pole piece.

8. The apparatus claimed in claim 1 further including resilient means for biasing said flux receiving and issuing means into preselected position relative to said flux coupler means.

9. The apparatus claimed in claim 8 wherein said flux coupler means and said flux receiving and issuing means include respective first and second plate members mutually pivotally moveable to effect such relative movement between said flux coupler means and said flux receiving and issuing means, said biasing means being operative on said first and second plate members.

10. The apparatus claimed in claim 9 wherein said second plate member is supported by said first plate member for such pivotal movement therebetween, said biasing means comprising a spring secured to each such plate member.

11. The apparatus claimed in claim 10 wherein said flux receiving and issuing means includes a pole piece for issuing said received flux in a predetermined direction, said spring providing bias force in a direction opposite the flux issuance direction of said pole piece.

12. The apparatus claimed in claim 1 wherein said transducer means comprises a coil having expanse in metal-free communication with the exterior of said apparatus.

13. In the method for testing objects by inducing therein an acoustic wave provided by radio frequency excitation of a transmitting coil while subjecting the object to a magnetic field provided by a magnetic field generator, the further steps of:
   (a) defining a path for movement of an object for testing;
   (b) supporting said coil and said generator for joint movement in a locus toward and from said path;
   (c) biasing said generator and said coil into a position distal from said path but wherein said generator has magnetic influence in said path; and
   (d) moving said object into said path to the vicinity of such joint movement locus,
      the force of such biasing in step (c) being selected to be less than the force of magnetic interaction between said generator and said object, whereby said coil and said generator are moved against such bias force under magnetic influence from such distal position into operative test position relative to said object.

* * * * *